US012778953B2

(12) United States Patent
Buschmann et al.

(10) Patent No.: US 12,778,953 B2
(45) Date of Patent: Nov. 3, 2026

(54) SODIUM 2-[(4S)-8-FLUORO-2-[4-(3-METHOXYPHENYL)PIPERAZIN-1-Y1]-3-[2-METHOXY-5-(TRIFLUOROMETHYL)PHENYL]-4H-QUINAZOLIN-4-YL]ACETATE AND PHARMACEUTICAL COMPOSITIONS THEREOF

(71) Applicant: AIC246 AG & Co. KG, Wuppertal (DE)

(72) Inventors: Helmut Buschmann, Aachen (DE); Thomas Goldner, Velbert (DE); Jessica Redmer, Monchengladbach (DE); Andrea Hawe, Munich (DE); Matthias Lucke, Munich (DE); Dorothea Hohmann, Hamburg (DE); Monica Rosa, Munich (DE)

(73) Assignee: AIC246 AG & Co. KG, Wuppertal (DE)

( * ) Notice: Subject to any disclaimer, the term of this patent is extended or adjusted under 35 U.S.C. 154(b) by 849 days.

(21) Appl. No.: 17/802,651

(22) PCT Filed: Mar. 1, 2021

(86) PCT No.: PCT/EP2021/055062

§ 371 (c)(1),
(2) Date: Aug. 26, 2022

(87) PCT Pub. No.: WO2021/170878

PCT Pub. Date: Sep. 2, 2021

(65) Prior Publication Data

US 2023/0095980 A1 Mar. 30, 2023

(30) Foreign Application Priority Data

Feb. 27, 2020 (EP) .................................... 20159699

(51) Int. Cl.
*A61K 31/517* (2006.01)
*A61K 9/19* (2006.01)

(52) U.S. Cl.
CPC .............. *A61K 31/517* (2013.01); *A61K 9/19* (2013.01)

(58) Field of Classification Search
CPC ............................ C07D 239/04; A61K 31/517
See application file for complete search history.

(56) References Cited

U.S. PATENT DOCUMENTS

| | | | | |
|---|---|---|---|---|
| 8,513,255 | B2 | 8/2013 | Wunberg et al. | |
| 2015/0038514 | A1* | 2/2015 | Grunenberg ......... | C07D 239/84 544/283 |
| 2015/0133461 | A1 | 5/2015 | Paulus et al. | |

FOREIGN PATENT DOCUMENTS

| | | | |
|---|---|---|---|
| CN | 104144917 | A | 11/2014 |
| CN | 109966244 | A | 7/2019 |
| JP | 2015508802 | A | 3/2015 |
| WO | 2013127970 | A1 | 9/2013 |
| WO | 2013127971 | A1 | 9/2013 |
| WO | 2014202737 | A1 | 12/2014 |
| WO | 2021170874 | A1 | 9/2021 |
| WO | 2021170875 | A1 | 9/2021 |
| WO | 2021170879 | A1 | 9/2021 |
| WO | 2021170882 | A1 | 9/2021 |

OTHER PUBLICATIONS

Search report in corresponding EP20159699.6 dated Aug. 31, 2020 (pp. 1-7).
International Search Report PCT/EP2021/055062 dated May 31, 2021 (pp. 1-3) and written opinion (pp. 1-7).
Wu Junke et al: "Guide to Key Technologies of Pharmaceutical Engineering", The Fourth Military Medical University Press, Xi'an City, 1st edition, Apr. 2008, pp. 280-282.
Rowe Raymond C. et al.: "Handbook of Pharmaceutical Excipients", 5th Edition, Pharmaceutical Press, American Pharmacists Association, 2006, pp. 535-536; 611-612.

* cited by examiner

*Primary Examiner* — Paul V Ward
(74) *Attorney, Agent, or Firm* — Millen, White, Zelano & Branigan, PC; Brion P. Heaney

(57) ABSTRACT

The present invention relates to new stable pharmaceutical compositions containing sodium 2-[(4S)-8-fluoro-2-[4-(3-methoxyphenyl)piperazin-1-yl]-3-[2-methoxy-5-(trifluoromethyl)-phenyl]-4H-quinazolin-4-yl]acetate that are essentially free of complexing solubilizing agents, such as PEG, cyclodextrin, lysin, arginine, in particular HPBCD. The invention further relates to methods of preparation of said pharmaceutical compositions. The invention further relates to use of said pharmaceutical compositions in methods of treatment of and/or as a prophylactic for illnesses, particularly its use as an antiviral, preferably against cytomegaloviruses.

48 Claims, No Drawings

SODIUM 2-[(4S)-8-FLUORO-2-[4-(3-METHOXYPHENYL)PIPERAZIN-1-Y1]-3-[2-METHOXY-5-(TRIFLUOROMETHYL)PHENYL]-4H-QUINAZOLIN-4-YL]ACETATE AND PHARMACEUTICAL COMPOSITIONS THEREOF

The present invention relates to new stable pharmaceutical compositions containing a sodium salt of 2-[(4S)-8-fluoro-2-[4-(3-methoxyphenyl)piperazin-1-yl]-3-[2-methoxy-5-(trifluoromethyl)phenyl]-4H-quinazolin-4-yl] acetate, also known as letermovir, that are suitable for oral and intravenous application and for injection. Said pharmaceutical compositions are essentially free from particular complexing solubilizing agents, such as PEG, cyclodextrin, lysine, arginine, in particular hydroxypropyl-β-cyclodextrin (HPBCD). Said formulations are suitable for use in methods of treatment of viral diseases, in particular human cytomegalovirus (hereinafter HCMV) infections. The invention also relates to methods of preparation of said pharmaceutical compositions.

BACKGROUND

Cytomegalovirus (CMV) is a common opportunistic infection that causes significant morbidity and preventable mortality after solid-organ and allogeneic hematopoietic stem cell transplantation.

HCMV is a species of virus that belongs to the viral family known as Herpesviridae or herpes viruses. It is typically abbreviated as HCMV and is alternatively known as human herpesvirus-5 (HHV-5). Within Herpesviridae, HCMV belongs to the Betaherpesvirinae subfamily, which also includes cytomegaloviruses from other mammals.

Letermovir is known as a highly active drug for addressing HCMV infection and extensively described in Lischka et al., *In Vitro and In Vivo Activities of the Novel Anticytomegalovirus Compound Letermovir. Antimicrob. Agents Chemother.* 2010, 54: p.1290-1297, and Kaul et al., *First report of successful treatment of multidrug-resistant cytomegalovirus disease with the novel anti-CMV compound Letermovir. Am. J. Transplant.* 2011, 11:1079-1084; as well as Marschall et al., *In Vitro Evaluation of the Activities of the Novel Anticytomegalovirus Compound Letermovir against Herpesviruses and Other Human Pathogenic Viruses. Antimicrob. Agents Chemother.* 2012, 56:1135-1137.

The chemical name of letermovir is 2-[(4S)-8-fluoro-2-[4-(3-methoxyphenyl)piperazin-1-yl]-3-[2-methoxy-5-(trifluoromethyl) phenyl]-4H-quinazolin-4-yl]acetic acid, and the chemical structure of letermovir is depicted below:

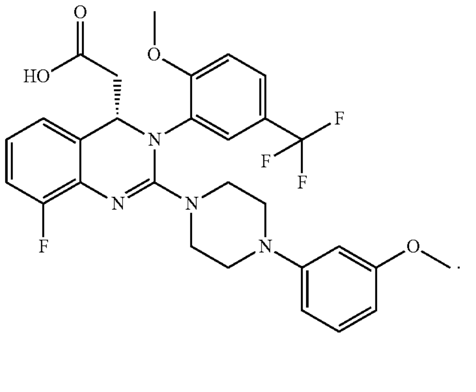 [SMILES: COc1cccc(N2CCN(C3=Nc4c(F)cccc4[C@H](CC(=O)O)N3c3cc(C(F)(F)F)ccc3OC)CC2)c1]

Letermovir was developed as an antiviral agent, in particular for the treatment, prevention, or prophylaxis of infections caused by the human cytomegalovirus (HCMV), and is disclosed in International Publication No. WO 2004/096778. In addition, salts of 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid were also prepared, as described in International Publication No. WO 2013/127971.

Liquid pharmaceutical formulations comprising amorphous letermovir are described in International Publication No. WO 2013/127970 which relates to a pharmaceutical composition that can be used in particular for intravenous administration, that contains letermovir, that has long-term stability and can be stored, and that in addition has a substantially physiological pH. It has further been discovered that such compositions can be lyophilized in order to obtain a stable, solid pharmaceutical composition that can be reconstituted in a simple manner for injection purposes, e.g. by adding water, as a result of which, in turn, a stable pharmaceutical composition, e.g. for intravenous administration, can be obtained.

There remains a need, however, for pharmaceutical compositions comprising letermovir having long-term stability at substantially physiological pH, that are suitable for use in subjects of all ages in the need of solid-organ transplantation, and allogenic hematopoietic stem cell transplantation. Moreover, the pharmaceutical composition comprising letermovir and complexing solubilizing agents, such as PEG, lysine, arginine, a cyclodextrin, in particular a hydroxypropyl-beta-cyclodextrin (HPBCD), have a tendency to cause particulate issues when being dissolved in a parenterally acceptable diluent, such as water, hence requiring additional work-up prior to the intended use, for example, filtering the pharmaceutical composition before administration. Therefore, there remains a need for ready-to-use particulate-free parenteral solutions comprising letermovir.

DESCRIPTION OF THE INVENTION

In a first aspect, the present invention relates to a pharmaceutical composition comprising a sodium salt of letermovir of formula (I)

(I)

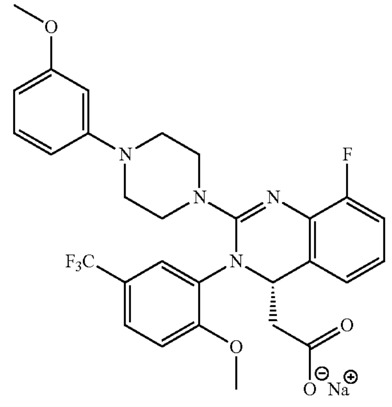

or a solvate thereof, wherein the composition is essentially free from a compound selected from the group consisting of PEG, lysine, arginine, a cyclodextrin, in particular a hydroxypropyl-beta-cyclodextrin (HPBCD).

These pharmaceutical compositions contain letermovir in a concentration sufficient to achieve the desired therapeutic effect, while having long-term stability, and a substantially physiological pH.

It has been further discovered that said pharmaceutical composition can be obtained in a form of a lyophilizate that can be fully reconstituted in a parenterally acceptable diluent, such as water, aqueous glucose solution or Ringer's lactate solution. Said lyophilizates exhibit surprisingly long-term stability and the reconstitutes in parenterally acceptable diluents have substantially physiological pH.

In another aspect, the present invention relates to a method for producing said pharmaceutical composition, comprising the following steps:

i) providing a solution of a sodium salt of letermovir or a solvate thereof and optionally at least one excipient selected from the group consisting of a carbohydrate, in particular sucrose and mannitol; an amino acid, in particular phenylalanine; a polyalkoxy compound, in particular a poloxamer, more particular poloxamer 188; and a polyvinylpyrrolidone (PVP), in particular PVP PF12;

ii) if needed, adjusting the pH of the solution obtained in step i) to a range of from 7 to 8, preferably with HCl;

iii) optionally, filtering said solution.

In particular, the method according to the invention may further comprise the subsequent steps of: freeze-drying the solution obtained in step iii above, to provide a lyophilizate and optionally reconstituting the lyophilizate in a first parenterally acceptable diluent to provide, a reconstituted solution in a concentration range of from 1 to 100 mg/mL, and optionally further diluting said reconstituted solution with a second parenterally acceptable diluent to a final concentration which is acceptable for injection or infusion, and wherein said first and said second parenterally acceptable diluents can be the same or different.

In another aspect, the present invention relates to the use of the pharmaceutical compositions described herein, for the preparation of a medication for the treatment and/or prevention of diseases, in particular of viral infections, preferably human cytomegalovirus (HCMV) infections or infections with another member of the herpes viridae group.

Another aspect of the present invention relates to a method for the treatment and/or prevention of virus infections, preferably human cytomegalovirus (HCMV) infections or infections with another member of the herpes viridae group, in a subject in need thereof by administering said pharmaceutical composition. In particular, the pharmaceutical composition according to the present inventions is suitable for treatment of neonates, subjects in the need of particular solid-organ transplantation, e.g. subjects with kidney damage and subjects in need of allogenic hematopoietic stem cell transplantation.

DETAILED DESCRIPTION

It is noted that the term "comprising" also encompasses the meaning "consisting of", e.g., a group of members comprising said members also encompasses a group of members consisting only of these members.

The term "room temperature" as used herein, is synonymous to the term "standard room temperature" and refers to a temperature in the range of from 19° C. to 26° C. For example, "stirring at room temperature" means "stirring at a temperature in the range of from 19° C. to 26° C.".

Within the scope of the invention the term "stability" is understood to mean not only the chemical stability of the constituents of the pharmaceutical composition, in particular, the active substance, but also the physicochemical stability of the composition itself. In particular, the composition according to the invention must be stable against precipitation of the constituents.

In this context, the term "stability" means that at 2° C. to 8° C., or at 25° C. or at 40° C. the pharmaceutical compositions according to the invention contain a minimum proportion of >90%, preferably >95%, and more preferably >98% of the active substance for a storage period of at least one month, preferably at least three months, even more preferably at least 6 months, even more preferably 12 months, even more preferably 18 months, and most preferred at least 36 months, when said liquid pharmaceutical composition is measured according to the HPLC method of the present invention.

Within the scope of the invention the term "solvates" refers to those forms of a sodium salt of Letermovir which form a complex through coordination with solvent molecules. Hydrates are a special form of solvates in which the coordination takes place with water. In particular, the sodium salt of Letermovir may be a monohydrate or trihydrate.

The term "cyclodextrin" as used herein, is understood to encompass any modified or non-modified cyclodextrin, in particular selected from α-cyclodextrins, β-cyclodextrins or γ-cyclodextrins. The examples of modified β-cyclodextrins include, in particular, hydroxyalkyl-β-cyclodextrins, e.g. hydroxymethyl-β-cyclodextrin, hydroxyethyl-β-cyclodextrin or hydroxyl-propyl-β-cyclodextrin, alkyl-hydroxyalkyl-β-cyclodextrins, e.g. methyl-hydroxypropyl-β-cyclodextrins or ethyl-hydroxypropyl-cyclodextrins or sulfoalkyl-cyclodextrins. Hydroxy-propyl-β-cyclodextrins are available in various degrees of substitution, in particular 2-hydroxypropyl-β-cyclodextrin is available as Cavasol® W7 HP, Cavitron® W7 HP5 and Cavitron® W7 HP7.

As used herein the term "complexing solubilizing agents" refers to the compounds which enhance solubility of the active ingredient of the pharmaceutical composition of the invention by forming coordination bonds between said compound and the molecule of the active ingredient, in particular in an aqueous solution, i.e. by actually and detectably forming a complex with the active ingredient of the pharmaceutical composition of the invention. The non-limiting examples of complexing solubilizing agents include non-polymeric solubilizers, such as lysine or arginine, and polymeric solubilizers, such as PEG or cyclodextrins.

As used herein the term "parenterally acceptable diluents", "parenteral admixture diluents" and "commercial diluents" refers to any liquid material which is used to dilute an active ingredient, which is suitable for administration to a subject by a route other than topical or oral. Examples of parenteral routes include intramuscular, intravascular (including intraarterial or intravenous), intraorbital, retrobulbar, intranasal, intrathecal, intraventricular, intraspinal, intraperitoneal, intrapulmonary, intracisternal, intracapsular, intrasternal, peribulbar, or intralesional administration. Examples of parenterally acceptable diluents include water, aqueous glucose solution or Ringer's lactate solution. Within the application the terms "commercial diluents", "parenteral admixture diluents" and "parenterally acceptable diluents" have the same meaning and are used interchangeably.

As used herein, the term "carbohydrate" refers to compounds that are polyhydroxy aldehydes or ketones, or substances that yield such compounds on hydrolysis. Some carbohydrates may further contain nitrogen, phosphorous, or sulfur. Examples of carbohydrates include monosaccharides, disaccharides, oligosaccharides, and polysaccharides, in particular sucrose or mannitol.

As used herein, the term "amino acid" refers to any of the twenty naturally occurring amino acids or their synthetic analogs with unnatural side chains and including both D and L optical isomers. The examples of amino acids include, in particular, alanine and phenylalanine.

As used herein, the term "polyalkoxy compounds" refers to the polymeric compounds in which the repeating units represent alkyl groups having straight or branched chain linked to an oxygen atom. The examples of polyalkoxy compounds include poloxamers, in particular, poloxamer 188.

Within the scope of the present invention the terms "obtained by" and "obtainable by" have the same meaning and are used interchangeably.

As used herein the term "aqueous solution" refers to liquid homogeneous mixtures comprising water.

As used herein, the terms "lyophilization" and "freeze-drying" are used interchangeably and mean a process by which a desired product containing a solvent, in particular water, is cooled to a sufficient temperature, in particular by using liquid nitrogen or cooled shelves, at which a portion or all of the solvent is frozen and the frozen solvent is further removed by one or more drying steps, in particular by removal of unbound solvent by sublimation and desorption. The terms "lyophilizate" and "freeze-dried product" refer to the product obtained by freeze-drying and are used interchangeably throughout the application.

As used herein, the term "reconstitution" or "reconstituting" refers to a process of dissolving a lyophilizate in a diluent, preferably in a parenterally acceptable diluent, in particular water. The term "reconstituted solution" refers to the product obtained by reconstitution.

As used herein, the term "liquid pharmaceutical composition" refers to a solution, suspension or dispersion of an active ingredient optionally in combination with one or more pharmaceutically acceptable excipients in a liquid. In particular, the liquid pharmaceutical composition refers to a solution of an active ingredient in combination with one or more pharmaceutically acceptable excipients in a physiologically acceptable diluent, particularly a parenterally acceptable diluent, such as water.

As used herein, the term "solid pharmaceutical composition" refers to a composition of an active ingredient optionally in combination with one or more pharmaceutically acceptable excipients in a solid state. In particular, the solid pharmaceutical composition refers to a lyophilizate comprising an active ingredient in combination with one or more pharmaceutically acceptable excipients.

As used herein the term "treatment" or "treating" is defined as the application or administration of a therapeutic agent i.e., a sodium salt of Letermovir or a solvate or a hydrate thereof (alone or in combination with another pharmaceutical agent) to a subject, or application or administration of a therapeutic agent to an isolated tissue or cell line from a subject who has an HCMV infection, a symptom of HCMV infection, or the potential to develop an HCMV infection with the purpose to cure, heal, alleviate, relieve, alter, remedy, ameliorate, improve or affect the HCMV infection, the symptoms of HCMV infection or the potential to develop an HCMV infection. Such treatments may be specifically tailored or modified based on knowledge obtained from the field of pharmacogenomics.

As used herein the term "prevent", "preventing" or "prevention" means no disorder or disease development if none had occurred, or no further disorder or disease development if there had already been development of the disorder or disease. Also considered is the ability of one to prevent some or all of the symptoms associated with the disorder or disease. Prevention of diseases encompasses prophylaxis of diseases.

As used herein the term "subject" refers to a human or a non-human mammal. Non-human mammals include for example livestock and pets such as ovine, bovine, porcine, feline, canines and murine mammals. Preferably the subject is human. In one embodiment, the subject is a human infant. In a preferred embodiment, the subject is a human neonate. In another preferred embodiment, the subject is a subject in the need of particular solid-organ transplantation, e.g. a subject with kidney damages and a subject in need of allogenic hematopoietic stem cell transplantation.

As used herein the term "pharmaceutically acceptable" refers to a material such as a carrier or diluent which does not abrogate the biological activity or properties of the compound and is relatively non-toxic; i.e., the material may be administered to a subject without causing undesirable biological effects or interacting in a deleterious manner with any of the components of the composition in which it is contained.

As used herein the term "essentially free" refers to a content of less than 5 mole %

The subject-matter of the present invention relates to a pharmaceutical composition comprising a sodium salt of letermovir of formula (I)

(I)

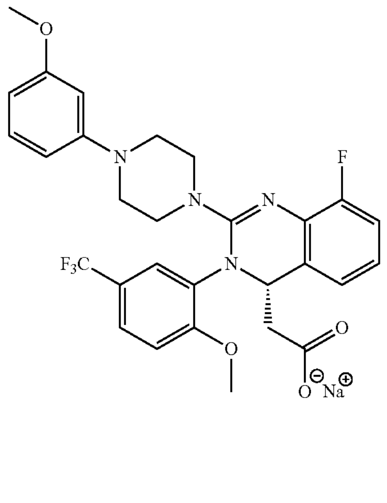

or a solvate thereof, wherein the composition is essentially free from a complexing solubilizing agent selected from the group consisting of PEG, lysine, arginine, and a cyclodextrin. In one embodiment, the cyclodextrin is a hydroxypropyl-beta-cyclodextrin (HPBCD).

In one embodiment a pharmaceutical composition according to the invention is a liquid pharmaceutical composition comprising a sodium salt of letermovir of formula (I)

(I)

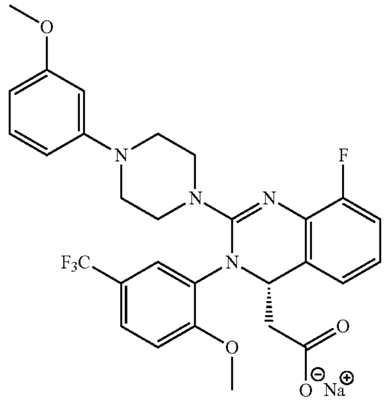

or a solvate thereof, dissolved in a physiologically acceptable diluent, particularly a parenterally acceptable diluent, wherein the liquid pharmaceutical composition is essentially free from a complexing solubilizing agent selected from the group consisting of PEG, lysine, arginine, and a cyclodextrin. In one embodiment, the cyclodextrin is a hydroxypropyl-beta-cyclodextrin (HPBCD).

In one embodiment a liquid pharmaceutical composition according to the invention is an aqueous solution. In one embodiment said liquid pharmaceutical composition according to the invention is a solution in at least one physiologically acceptable diluent. A physiologically acceptable diluent is a pharmaceutically acceptable diluent and is, in particular, an orally acceptable diluent, i.e., a diluent acceptable for oral application or a parenterally acceptable diluent, i.e. a diluent acceptable for parenteral application. Non-limiting examples of parenterally acceptable diluents include water, aqueous glucose solution and Ringer's lactate solution.

In one embodiment, a liquid pharmaceutical composition according to the invention is essentially free from a compound selected from the group consisting of PEG, lysine, arginine, and a cyclodextrin. In one embodiment a liquid pharmaceutical composition according to the invention is essentially free from lysine. In another embodiment a liquid pharmaceutical composition according to the invention is essentially free from arginine. In yet another embodiment a liquid pharmaceutical composition according to the invention is essentially free from PEG. In yet another embodiment a liquid pharmaceutical composition according to the invention is essentially free from a cyclodextrin. In a preferred embodiment a liquid pharmaceutical composition according to the invention is essentially free from hydroxypropyl-beta-cyclodextrin. In another preferred embodiment a liquid pharmaceutical composition according to the invention is essentially free from PEG, lysine, arginine and a cyclodextrin, in particular a hydroxypropyl-beta-cyclodextrin (HPBCD).

In one embodiment a liquid pharmaceutical composition according to the invention is essentially free from complexing solubilizing agents, in particular essentially free from PEG, lysine, arginine, and a cyclodextrin, in particular a hydroxypropyl-beta-cyclodextrin (HPBCD).

In one embodiment a liquid pharmaceutical composition according to the invention is essentially free from any additional buffer.

In one embodiment, the content of complexing solubilizing agents in a liquid pharmaceutical composition according to the invention is less than 5 mole %. In a preferred embodiment, the content of complexing solubilizing agents in a liquid pharmaceutical composition according to the invention is less than 3 mole %. In a more embodiment, the content of complexing solubilizing agents in a liquid pharmaceutical composition according to the invention is less than 1 mole %. In a more preferred embodiment, the content of complexing solubilizing agents in a liquid pharmaceutical composition according to the invention is less than 0.5 mole %. Most preferred, the content of complexing solubilizing agents in a liquid pharmaceutical composition according to the invention is less than 0.3 mole %.

In one embodiment a liquid pharmaceutical composition comprising a sodium salt of letermovir of formula (I)

(I)

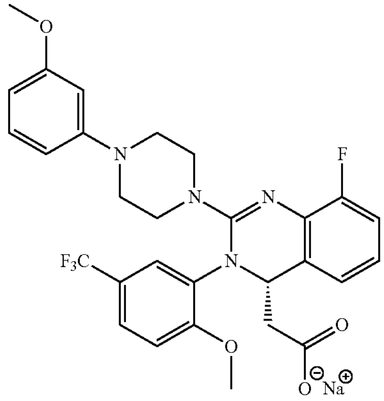

or a solvate thereof, wherein the liquid composition is essentially free from complexing solubilizing agents selected from the group consisting of PEG, lysine, arginine, a cyclodextrin, in particular a hydroxypropyl-beta-cyclodextrin (HPBCD), further comprises at least one pharmaceutical carrier or excipient.

In one embodiment a liquid pharmaceutical composition according to the invention comprises at least one excipient selected from the group consisting of a carbohydrate, such as sucrose or mannitol; an amino acid, such as phenylalanine; a polyalkoxy compound, such as a poloxamer, such as poloxamer 188; and a polyvinylpyrrolidone (PVP), such as PVP PF12. In a preferred embodiment said excipient is mannitol or sucrose or a combination thereof.

In one embodiment a liquid pharmaceutical composition according to the invention is essentially free from complexing solubilizing agents.

In one embodiment a liquid pharmaceutical composition according to the invention may contain an excipient which exhibits complexing solubilizing properties. In one embodiment such an excipient is a polyalkoxy compound, such as a poloxamer. In one embodiment, the poloxamer is poloxamer 188.

In one embodiment, the liquid pharmaceutical composition according to the invention comprises a polyalkoxy compound, a poloxamer, or particularly poloxamer 188, and is essentially free from other complexing solubilizing agents.

In one embodiment the used excipients are suitable for administration to subjects in the need of particular solid-organ transplantation, e.g. subjects with kidney damages. Non-limiting examples of such excipients include sucrose, mannitol, phenylalanine, and a poloxamer, such as particular poloxamer 188, and a polyvinylpyrrolidone (PVP), such as PVP PF12.

In one embodiment a liquid pharmaceutical composition according to the invention further comprises a buffer, preferably Tris hydroxy aminomethane (Tris).

In one embodiment a liquid pharmaceutical composition according to the invention further comprises HCl. In another embodiment, HCl is used to adjust the pH of the liquid pharmaceutical composition.

In a preferred embodiment a liquid pharmaceutical composition according to the invention has a pH in the range of from 7 to 8. In a more preferred embodiment a liquid pharmaceutical composition according to the invention has a pH in the range of from 7.4 to 7.8.

In one embodiment said liquid pharmaceutical composition according to the invention is suitable for oral application.

In one embodiment a pharmaceutical composition according to the invention is in a solid form. In a preferred embodiment said solid form of said pharmaceutical composition is a lyophilizate.

Preferably said solid form of said pharmaceutical composition is obtainable by freeze-drying the liquid pharmaceutical composition as defined in any of the preceeding embodiments.

In one embodiment a solid form of a pharmaceutical composition according to the invention comprises the sodium salt of letermovir or a solvate thereof, which is in the amorphous form. In one embodiment a solid form of a pharmaceutical composition according to the invention comprises the sodium salt of letermovir which is a crystalline monohydrate or a crystalline trihydrate.

In one embodiment a solid pharmaceutical composition according to the invention is essentially free from a complexing solubilizing agent selected from the group consisting of PEG, lysine, arginine, and a cyclodextrin. In one embodiment, the cyclodextrin is a hydroxypropyl-beta-cyclodextrin (HPBCD).

In one embodiment, a solid pharmaceutical composition according to the invention is essentially free from a compound selected from the group consisting of PEG, lysine, arginine, and a cyclodextrin. In one embodiment a solid pharmaceutical composition according to the invention is essentially free from lysine. In another embodiment a solid pharmaceutical composition according to the invention is essentially free from arginine. In yet another embodiment a solid pharmaceutical composition according to the invention is essentially free from PEG. In yet another embodiment a solid pharmaceutical composition according to the invention is essentially free from a cyclodextrin. In a preferred embodiment a solid pharmaceutical composition according to the invention is essentially free from hydroxypropyl-beta-cyclodextrin. In another preferred embodiment a solid pharmaceutical composition according to the invention is essentially free from PEG, lysine, arginine and a cyclodextrin, in particular a hydroxypropyl-beta-cyclodextrin (HPBCD).

In one embodiment a solid pharmaceutical composition according to the invention is essentially free from complexing solubilizing agents, in particular essentially free from PEG, lysine, arginine, and a cyclodextrin, in particular a hydroxypropyl-beta-cyclodextrin (HPBCD).

In one embodiment a solid pharmaceutical composition according to the invention is essentially free from any additional buffer.

In one embodiment, the content of complexing solubilizing agents in a solid pharmaceutical composition according to the invention is less than 5 mole %. In a preferred embodiment, the content of complexing solubilizing agents in a solid pharmaceutical composition according to the invention is less than 3 mole %. In a more preferred embodiment, the content of complexing solubilizing agents in a solid pharmaceutical composition according to the invention is less than 1 mole %. In a more preferred embodiment, the content of complexing solubilizing agents in a solid pharmaceutical composition according to the invention is less than 0.5 mole %. Most preferred, the content of complexing solubilizing agents in a solid pharmaceutical composition according to the invention is less than 0.3 mole %.

In one embodiment a solid pharmaceutical composition comprising a sodium salt of letermovir of formula (I)

(I)

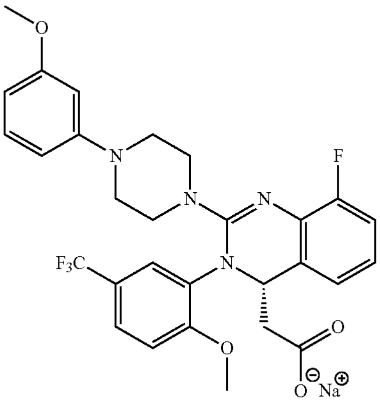

or a solvate thereof, wherein the solid pharmaceutical composition is essentially free from complexing solubilizing agents selected from the group consisting of PEG, lysine, arginine, a cyclodextrin, in particular a hydroxypropyl-beta-cyclodextrin (HPBCD), further comprises at least one pharmaceutical carrier or excipient.

In one embodiment a solid pharmaceutical composition according to the invention comprises at least one excipient selected from the group consisting of a carbohydrate, such as sucrose or mannitol; an amino acid, such as phenylalanine; a polyalkoxy compound, such as a poloxamer, such as poloxamer 188; and a polyvinylpyrrolidone (PVP), such as PVP PF12. In a preferred embodiment said excipient is mannitol or sucrose or a combination thereof.

In one embodiment a solid pharmaceutical composition according to the invention is essentially free from complexing solubilizing agents.

In one embodiment a solid pharmaceutical composition according to the invention may contain an excipient which exhibits complexing solubilizing properties. In one embodiment such an excipient is a polyalkoxy compound, such as a poloxamer. In one embodiment, the poloxamer is poloxamer 188.

In one embodiment, the solid pharmaceutical composition according to the invention comprises a polyalkoxy compound, a poloxamer, or particularly poloxamer 188, and is essentially free from other complexing solubilizing agents.

In one embodiment the used excipients are suitable for administration to subjects in the need of particular solid-organ transplantation, e.g. subjects with kidney damages. Non-limiting examples of such excipients include sucrose, mannitol, phenylalanine, and a poloxamer, such as particular poloxamer 188, and a polyvinylpyrrolidone (PVP), such as PVP PF12.

In one embodiment a solid pharmaceutical composition according to the invention further comprises a buffer, preferably Tris hydroxy aminomethane (Tris).

In a preferred embodiment said solid pharmaceutical composition according to the invention has a pH of from 7 to 8 after being dissolved in a parenterally acceptable diluent without any additional buffer. In a more preferred embodiment said solid pharmaceutical formulation has a pH in the range of from 7.4 to 7.8 after being dissolved in a parenterally acceptable diluent without any additional buffer. In one embodiment said solid pharmaceutical composition optionally further comprises HCl.

In a preferred embodiment said solid pharmaceutical composition is capable of providing a solution when being dissolved in water without any additional buffer and without any additional complexing solubilizing agents selected from the group consisting of PEG, lysine, arginine, a cyclodextrin, in particular a hydroxypropyl-beta-cyclodextrin (HPBCD), wherein said solution comprises the sodium salt of letermovir or the solvate thereof at a concentration in the range of from 20 to 100 mg/mL with respect to letermovir free base and exhibits a pH in the range of from 7 to 8, preferably 7.4 to 7.8.

In a preferred embodiment said solid pharmaceutical composition:

is essentially free from complexing solubilizing agents selected from the group consisting of PEG, lysine, arginine, a cyclodextrin, in particular a hydroxypropyl-beta-cyclodextrin (HPBCD), and is capable of providing a solution when being dissolved in water without any additional buffer and without any additional complexing solubilizing agents selected from the group consisting of PEG, lysine, arginine, a cyclodextrin, in particular a hydroxypropyl-beta-cyclodextrin (HPBCD), wherein said solution comprises the sodium salt of letermovir or the solvate thereof at a concentration in the range of from 20 to 100 mg/mL with respect to letermovir free base and exhibits a pH in the range of from 7 to 8, preferably 7.4 to 7.8.

In one embodiment a pharmaceutical composition according to the invention is a liquid pharmaceutical composition comprising the solid pharmaceutical composition as defined in any of the preceeding embodiments dissolved in a parenterally acceptable diluent which is essentially free from complexing solubilizing agents selected from the group consisting of PEG, lysine, arginine, a cyclodextrin, in particular a hydroxypropyl-beta-cyclodextrin (HPBCD). Preferably said liquid pharmaceutical composition comprises the sodium salt of letermovir or the solvate thereof at a concentration in the range of from 20 to 100 mg/mL with respect to letermovir free base.

In one embodiment a liquid pharmaceutical composition comprising the solid pharmaceutical composition as defined in any of the preceeding embodiments dissolved in a first parenterally acceptable diluent which is essentially free from complexing solubilizing agents selected from the group consisting of PEG, lysine, arginine, a cyclodextrin, in particular a hydroxypropyl-beta-cyclodextrin (HPBCD), at a concentration in the range of from 20 to 100 mg/mL with respect to Letermovir free base, is further diluted in a second parenterally acceptable diluent which is essentially free from complexing solubilizing agents selected from the group consisting of PEG, lysine, arginine, a cyclodextrin, in particular a hydroxypropyl-beta-cyclodextrin (HPBCD), to a concentration which is acceptable for intravenous (IV) injection or infusion, wherein said first and said second parenterally acceptable diluents can be identical or different from each other.

In one embodiment a pharmaceutical composition according to the invention is a liquid pharmaceutical composition comprising the solid pharmaceutical composition as defined in any of the preceeding embodiments dissolved in water. In one embodiment a pharmaceutical composition according to the invention is a liquid pharmaceutical composition comprising the solid pharmaceutical composition as defined in any of the preceeding embodiments dissolved in in at least one parenterally acceptable diluent. Non-limiting examples of parenterally acceptable diluents include water, aqueous glucose solution and Ringer's lactate solution. In a preferred embodiment said liquid pharmaceutical composition according to the invention has a pH in the range of from 7 to 8. In a more preferred embodiment said liquid pharmaceutical composition according to the invention has a pH in the range of from 7.4 to 7.8. In one embodiment the concentration of the sodium salt of letermovir or a solvate thereof in said liquid pharmaceutical composition according to the invention is in the range of from 1 to 100 mg/mL. In a preferred embodiment the concentration of the sodium salt of letermovir or a solvate thereof in said liquid pharmaceutical composition according to the invention is in the range of from 20 to 100 mg/mL.

Within the scope of the present invention mass concentrations are given with respect to letermovir free base. In particular, 20 mg/mL with respect to letermovir free base means that the molar concentration of the sodium salt of letermovir or a solvate thereof shall be equal to the molar concentration of letermovir free base which corresponds to the mass concentration of 20 mg/mL of letermovir free base. For example, the molar mass of a trihydrate of the sodium salt of letermovir is 650.6 g/mol. The molar mass of letermovir free base is 572.6 g/mol. In this regard the mass concentration of 20 mg/mL with respect to letermovir free base corresponds to the mass concentration of $20 \cdot 650.6/572.6 = 22.7$ mg/mL with respect to a trihydrate of the sodium salt of letermovir.

In one embodiment said liquid pharmaceutical composition comprising the solid pharmaceutical composition as defined in any of the preceeding embodiments dissolved in at least one parenterally acceptable diluent, such as water, is suitable for intravenous (IV) application, i.e., for intravenous infusion or injection.

In one embodiment a pharmaceutical composition according to the invention represents a stability in accordance with ICH Q1A (R2) (Stability testing of new drug substances and drug products) covering the climate zones I to IV. In a preferred embodiment a pharmaceutical composition according to the invention as defined in any of the preceeding embodiments is stable for at least one month In a more preferred embodiment a pharmaceutical composition according to the invention as defined in any of the preceeding embodiments is stable for at least three months. In a more preferred embodiment a pharmaceutical composition according to the invention as defined in any of the preceeding embodiments is stable for at least 6 months. In a more preferred embodiment a pharmaceutical composition according to the invention as defined in any of the preceeding embodiments is stable for at least 12 months. In a more preferred embodiment a pharmaceutical composition according to the invention as defined in any of the preceeding embodiments is stable for at least 18 months. In a more preferred embodiment a pharmaceutical composition according to the invention as defined in any of the preceeding embodiments is stable for at least 36 months.

The subject-matter of the present invention further relates to a method for producing the pharmaceutical composition according to the invention, comprising the following steps:

i) providing a solution of a sodium salt of Letermovir or a solvate thereof and optionally at least one excipient selected from the group consisting of a carbohydrate, in particular sucrose and mannitol, an amino acid, in particular phenylalanine, a polyalkoxy compound, in particular a poloxamer, more particular poloxamer 188, and a polyvinylpyrrolidone (PVP), in particular PVP PF12.

In one embodiment the solution provided in step i above is a solution in a physiologically acceptable diluent, particularly a parenterally acceptable diluent, such as water.

In one embodiment the solution provided in step i above is essentially free from any additional buffer and any complexing solubilizing agents selected from the group consisting of PEG, lysine, arginine, a cyclodextrin, in particular a hydroxypropyl-beta-cyclodextrin (HPBCD).

In one embodiment providing a solution according to step i above comprises the following steps:

a-1) dissolving a trihydrate of the sodium salt of Letermovir in a parenterally acceptable diluent, in particular water;

b-1) adding at least one excipient selected from the group consisting of a carbohydrate, in particular selected from sucrose and mannitol, an amino acid, in particular phenylalanine, a polyalkoxy compound, in particular a poloxamer, more particular poloxamer 188, and a polyvinylpyrrolidone (PVP), in particular PVP PF12 to the solution obtained in step a-1;

c-1) optionally stirring said solution for at least 30 min.

In a preferred embodiment, the solution in step c-1 is stirred for at least 2 hours.

In another embodiment the method for providing a solution according to step i comprises utilizing the following steps a-2 to c-2, in place of steps a-1 to c-1 a-2) dissolving at least one excipient selected from the group consisting of a carbohydrate, in particular selected from sucrose and mannitol, an amino acid, in particular phenylalanine, a polyalkoxy compound, in particular a poloxamer, more particular poloxamer 188, and a polyvinylpyrrolidone (PVP), in particular PVP PF12n a parenterally acceptable diluent, in particular water;

b-2) adding a trihydrate of the sodium salt of letermovir in water to the solution obtained in step a-2;

c-2) optionally stirring said solution for at least 30 min.

In a preferred embodiment, the solution in step c-2 is stirred for at least 2 hours.

In a preferred embodiment a method for producing the pharmaceutical composition according to the present invention further comprises adjusting the pH of the solution obtained in step i to a range of from 7 to 8. In a more preferred embodiment a method for producing the pharmaceutical composition according to the present invention further comprises adjusting the pH of the solution obtained in step i to a range of from 7.4 to 7.8. In a preferred embodiment said adjustment is performed by adding HCl. In some embodiments the pH of the solution obtained in step i is in the range of 7 to 8, more preferred in the range of from 7.4 to 7.8 and the pH adjustment is not necessary.

In one embodiment the solution obtained after the pH adjustment is optionally stirred for at least 10 min, preferably at least 30 min.

In one embodiment a method for producing the pharmaceutical composition according to the present invention optionally comprises filtering the solution obtained in step i. In one embodiment a method for producing the pharmaceutical composition according to the present invention optionally comprises filtering the solution obtained after adjustment of the pH of the solution obtained in step i above.

In some embodiments the sodium salt of letermovir used in step i is in the amorphous form or the solvate of the sodium salt of letermovir or is a crystalline monohydrate or a crystalline trihydrate.

In one embodiment a method for producing the pharmaceutical composition according to the present invention further comprises freeze-drying the obtained solution to provide a lyophilizate.

In one embodiment a method for producing the pharmaceutical composition according to the present invention further comprises reconstituting the lyophilizate in a first parenterally acceptable diluent to provide a reconstituted solution in a concentration range of from 0.1 to 100 mg/mL with respect to letermovir free base and optionally further diluting said reconstituted solution with a second parenterally acceptable diluent to a final concentration which is acceptable for injection or infusion. Said first and said second parenterally acceptable diluents can be the same or different.

In one embodiment the final concentration which is acceptable for injection or infusion is in a range from 0.1 to 100 mg/mL. In a another embodiment the final concentration which is acceptable for injection or infusion is in a range from 0.8 to 100 mg/mL. In another embodiment the final concentration which is acceptable for injection or infusion is in a range from 20 to 100 mg/mL. In another embodiment the final concentration which is acceptable for injection or infusion is in a range from 50 to 100 mg/mL. In another embodiment the final concentration which is acceptable for injection or infusion is in a range from 20 to 50 mg/mL. In a preferred embodiment the final concentration which is acceptable for injection or infusion is 0.8 mg/mL.

In a preferred embodiment a method for producing the pharmaceutical composition according to the present invention comprises the following steps:

i) providing a solution of a sodium salt of letermovir or a solvate thereof and optionally at least one excipient selected from the group consisting of a carbohydrate such as sucrose or mannitol; an amino acid, such as phenylalanine; a polyalkoxy compound, such as a poloxamer, particularly poloxamer 188; and a polyvinylpyrrolidone (PVP), such as PVP PF12;

ii) if needed adjusting the pH of the solution obtained in step i) to a range of from 7 to 8 with a suitable organic or inorganic acid;

iii) optionally filtering the obtained solution.

In one embodiment of step ii the organic or inorganic acid is HCl.

In another preferred embodiment a method for producing the pharmaceutical composition according to the present invention comprises the following steps:

i) providing a solution of a sodium salt of letermovir or a solvate thereof and optionally at least one excipient selected from the group consisting of a carbohydrate, such as sucrose or mannitol; an amino acid, such as phenylalanine; a polyalkoxy compound, such as a poloxamer, particularly poloxamer 188; and a polyvinylpyrrolidone (PVP), such as PVP PF12;

ii) if needed adjusting the pH of the solution obtained in step i to a range of from 7 to 8 with a suitable organic or inorganic acid;

iii) optionally filtering the obtained solution;

iv) freeze-drying the obtained solution to provide a lyophilizate.

In one embodiment of step ii the organic or inorganic acid is HCl.

In another preferred embodiment a method for producing the pharmaceutical composition according to the present invention comprises the following steps:

i) providing a solution of a sodium salt of Letermovir or a solvate thereof and optionally at least one excipient selected from the group consisting of a carbohydrate, in particular selected from sucrose and mannitol, an amino acid, in particular phenylalanine, polyalkoxy compounds, in particular poloxamer, more particular poloxamer 188, and polyvinylpyrrolidone (PVP), in particular PVP PF12;

ii) if needed adjusting the pH of the solution obtained in step i to a range of from 7 to 8 with a suitable organic or inorganic acid;

iii) optionally filtering the obtained solution;

iv) freeze-drying the obtained solution to provide a lyophilizate;

v) reconstituting the lyophilizate in a first parenterally acceptable diluent to provide a reconstituted solution in a concentration range of from 1 to 100 mg/mL and optionally further diluting said reconstituted solution with a second parenterally acceptable diluent to a final concentration which is acceptable for injection or infusion, wherein said first and said second parenterally acceptable diluents can be the same or different.

In one embodiment of step ii the organic or inorganic acid is HCl.

In a preferred embodiment a method for producing the pharmaceutical composition according to the present invention comprises the following steps:

i) providing a solution of a sodium salt of letermovir or a solvate thereof and at least one excipient selected from the group consisting of a carbohydrate, in particular selected from sucrose and mannitol, an amino acid, in particular phenylalanine, a polyalkoxy compound, in particular a poloxamer, more particular poloxamer 188, and a polyvinylpyrrolidone (PVP), in particular PVP PF12, in a physiologically acceptable diluent, particularly a parenterally acceptable diluent, wherein said solution is essentially free from any additional buffer and any complexing solubilizing agents selected from the group consisting of PEG, lysine, arginine, a cyclodextrin, in particular a hydroxypropyl-beta-cyclodextrin (HPBCD);

ii) if needed adjusting the pH of the solution obtained in step i to a range of from 7 to 8 preferably with HCl;

iii) optionally filtering the obtained solution.

In a preferred embodiment a method for producing the pharmaceutical composition according to the present invention comprises the following steps:

i) providing a solution of a sodium salt of letermovir or a solvate thereof and at least one excipient selected from the group consisting of a carbohydrate, in particular selected from sucrose and mannitol, an amino acid, in particular phenylalanine, a polyalkoxy compound, in particular a poloxamer, more particular poloxamer 188, and a polyvinylpyrrolidone (PVP), in particular PVP PF12, in a physiologically acceptable diluent, particularly a parenterally acceptable diluent, wherein said solution is essentially free from any additional buffer and any complexing solubilizing agents selected from the group consisting of PEG, lysine, arginine, a cyclodextrin, in particular a hydroxypropyl-beta-cyclodextrin (HPBCD);

ii) if needed adjusting the pH of the solution obtained in step i to a range of from 7 to 8 preferably with HCl;

iii) optionally filtering the obtained solution;

iv) freeze-drying the obtained solution to provide a lyophilizate.

In a preferred embodiment a method for producing the pharmaceutical composition according to the present invention comprises the following steps:

i) providing a solution of a sodium salt of letermovir or a solvate thereof and at least one excipient selected from the group consisting of a carbohydrate, in particular selected from sucrose and mannitol, an amino acid, in particular phenylalanine, a polyalkoxy compound, in particular a poloxamer, more particular poloxamer 188, and a polyvinylpyrrolidone (PVP), in particular PVP PF12, in a physiologically acceptable diluent, particularly a parenterally acceptable diluent, wherein said solution is essentially free from any additional buffer and any complexing solubilizing agents selected from the group consisting of PEG, lysine, arginine, a cyclodextrin, in particular a hydroxypropyl-beta-cyclodextrin (HPBCD);

ii) if needed adjusting the pH of the solution obtained in step i to a range of from 7 to 8 preferably with HCl;

iii) optionally filtering the obtained solution;

iv) freeze-drying the obtained solution to provide a lyophilizate;

v) reconstituting said lyophilizate in a parenterally acceptable diluent which is essentially free from complexing solubilizing agents selected from the group consisting of PEG, lysine, arginine, a cyclodextrin, in particular a hydroxypropyl-beta-cyclodextrin (HPBCD).

The above steps i to v do not necessarily signify a specific sequence or number of steps. However, preferably the steps of the method are implemented in the order as shown above. Some of said steps may be optional and in some embodiments, optional steps are not implemented. For example in one embodiment step ii may directly be followed by step iv without implementation of step iii. Also the above shown steps do not exclude additional steps that are not explicitly mentioned. For example, the solution obtained in step i and/or ii may be optionally stirred.

The subject-matter of the present invention further relates to a pharmaceutical composition, which is obtainable by any method disclosed herein. In particular, the subject-matter of the present invention relates to a liquid pharmaceutical composition obtained by a method comprising steps i to iii as defined in any of the preceeding embodiments. The subject-matter of the present invention further relates to a solid pharmaceutical composition obtained by a method comprising steps i to iv as defined in any of the preceeding embodiments. The subject-matter of the present invention further relates to a liquid pharmaceutical composition comprising the solid pharmaceutical composition dissolved in a parenterally acceptable diluent obtained by a method comprising steps i to v as defined in any of the preceeding embodiments.

The pharmaceutical compositions according to the invention may be used to produce drugs which are suitable for use in methods of preventing and/or treating infections with a representative of the Herpes viridae group, in particular a cytomegalovirus, in particular the human cytomegalovirus.

In another aspect, the present invention relates to the pharmaceutical compositions according to the invention for use in a method of treating and/or preventing diseases, preferably viral infections, in particular infections with the human cytomegalovirus (HCMV) or another representative of the Herpes viridae group.

An additional aspect of the present invention relates to the use of the pharmaceutical compositions according to the invention in a method of treating and/or preventing diseases, preferably viral infections, in particular infections with the human cytomegalovirus (HCMV) or another representative of the Herpes viridae group.

Another aspect of the present invention relates to the use of the pharmaceutical compositions according to the invention for the preparation of a medicament for the treatment and/or preventing of diseases, in particular of viral infections, preferably human cytomegalovirus (HCMV) infections or infections with another member of the herpes viridae group.

Still another aspect of the present invention relates to a method for the treatment and/or prevention of virus infections, preferably human cytomegalovirus (HCMV) infections or infections with another member of the herpes viridae group, in a subject in need thereof by administering a pharmaceutical composition according to the invention. In one embodiment said subject is selected from the group consisting of neonates, subjects in the need of particular solid-organ transplantation, e.g. subjects with kidney damages and subjects in need of allogenic hematopoietic stem cell transplantation.

In general, it has proved to be advantageous to administer the pharmaceutical compositions in such a way that about 0.001 to 10 mg per kg, preferably 0.01 to 5 mg per kg body weight of 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid (letermovir) is administered.

Nevertheless, it may be necessary to deviate from the stated amounts of letermovir, namely depending on body weight, individual response to the active substance and the time and interval at which it is administered. For example, in certain cases it may be sufficient to administer less than the aforementioned minimum amount of letermovir, while in other cases the stated upper limit may be be exceeded. When administering large amounts it may be recommendable to distribute these in several individual doses over the course of a day.

With the above context, the following consecutively numbered embodiments provide further specific aspects of the invention:

1. A pharmaceutical composition comprising a sodium salt of letermovir of formula (I)

(I)

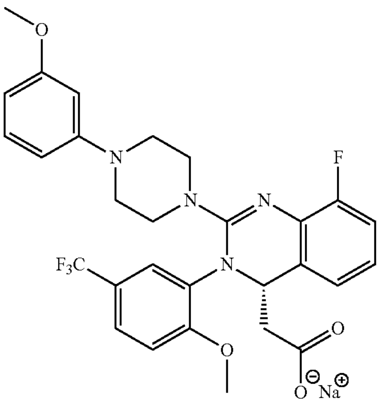

or a solvate thereof, wherein the composition is essentially free from complexing solubilizing agents selected from the group consisting of PEG, lysine, arginine, a cyclodextrin, in particular a hydroxypropyl-beta-cyclodextrin (HPBCD).
2. The pharmaceutical composition according to embodiment 1, further comprising at least one excipient selected from the group consisting of a carbohydrate, in particular selected from sucrose and mannitol, an amino acid, in particular phenylalanine, a polyalkoxy compound, in particular a poloxamer, more particular poloxamer 188, and a polyvinylpyrrolidone (PVP), in particular PVP PF12.
3. The pharmaceutical composition according to embodiment 1, wherein the pharmaceutical composition is essentially free from complexing solubilizing agents.
4. The pharmaceutical composition according to any one of embodiments 1 or 2, wherein the pharmaceutical composition comprises a polyalkoxy compound, in particular a poloxamer, more particular poloxamer 188, and is essentially free from other complexing solubilizing agents.
5. The pharmaceutical composition according to embodiment 2, wherein the excipient is mannitol or sucrose or a combination thereof.
6. The pharmaceutical composition according to any one of embodiments 1 to 5, further comprising a buffer, preferably Tris hydroxy aminomethane (Tris).
7. The pharmaceutical composition according to any one of embodiments 1 to 6 further comprising HCl.
8. The pharmaceutical composition according to any one of embodiments 1 to 7 which is in a solid form.
9. The pharmaceutical composition according to embodiment 8, wherein the sodium salt of letermovir is in the amorphous form.
10. The pharmaceutical composition according to embodiment 8 or 9, wherein, after being dissolved in a parenterally acceptable diluent, the solid form of said pharmaceutical formulation has a pH of from 7 to 8 and wherein said pharmaceutical composition optionally further comprises HCl.
11. The pharmaceutical composition according to any one of embodiments 1 to 7, wherein said pharmaceutical composition is in a liquid form.
12. The pharmaceutical composition according to any one of embodiments 1 to 11, wherein said pharmaceutical composition is in an oral dosage form.

13. The pharmaceutical composition according to embodiment 11, wherein the liquid form of said pharmaceutical composition is suitable for intravenous (IV) application or injection.
14. The pharmaceutical composition according to embodiment 11 or 13 having a pH in the range of from 7 to 8.
15. The pharmaceutical composition according to any one of embodiments 11 to 14 wherein the concentration of the sodium salt of letermovir or the solvate thereof in said pharmaceutical composition is in the range of from 1 to 100 mg/mL, preferably 20 to 100 mg/mL with respect to Letermovir free base.
16. The pharmaceutical composition according to any one of embodiments 1 to 15, having a stability in accordance with ICH Q1A (R2) covering the climate zones I to IV.
17. The pharmaceutical composition according to any one of embodiments 8 to 10, wherein the solid form of said pharmaceutical composition is a lyophilizate.
18. A method for producing the pharmaceutical composition as defined in any one of embodiments 1 to 17, comprising the following steps:
i) providing a solution of a sodium salt of letermovir or a solvate thereof and optionally at least one excipient selected from the group consisting of a carbohydrate, in particular selected from sucrose and mannitol, an amino acid, in particular phenylalanine, a polyalkoxy compound, in particular a poloxamer, more particular poloxamer 188, and a polyvinylpyrrolidone (PVP), in particular PVP PF12;
ii) if needed adjusting the pH of the solution obtained in step i) to a range of from 7 to 8 preferably with HCl;
iii) optionally filtering the obtained solution.
19. The method according to embodiment 18 wherein the sodium salt of letermovir is in the amorphous form or is a crystalline monohydrate or a crystalline trihydrate.
20. The method according to embodiment 18 or 19, further comprising the subsequent additional step of freeze-drying the obtained solution to provide a lyophilizate.
21. The method according to embodiment 20, further comprising the subsequent additional step of reconstituting the lyophilizate in a first parenterally acceptable diluent to provide a reconstituted solution in a concentration range of from 1 to 100 mg/mL and optionally further diluting said reconstituted solution with a second parenterally acceptable diluent to a final concentration which is acceptable for injection or infusion, wherein said first and said second parenterally acceptable diluents can be identical or different from each other.
22. The pharmaceutical composition according to any one of embodiments 1 to 17, which is obtainable by the method according to any one of embodiments 18 to 20.
23. The pharmaceutical composition according to any one of embodiments 1 to 16 or 22 for use in a method of treatment and/or prevention of diseases, in particular of virus infections, preferably human cytomegalovirus (HCMV) infections or infections with another member of the herpes viridae group.
24. The use of a pharmaceutical composition according to any one of embodiments 1 to 16 or 22 for the preparation of a medicament for the treatment and/or prevention of diseases, in particular of virus infections, preferably human cytomegalovirus (HCMV) infections or infections with another member of the herpes viridae group.
25. A method for the treatment and/or prevention of virus infections, preferably human cytomegalovirus (HCMV) infections or infections with another member of the herpes viridae group, in a subject in need thereof by administering a pharmaceutical composition according to any one of embodiments 1 to 16 or 22.

The invention will now be described in detail on the basis of non-restrictive examples.

Unless otherwise stated, the percentages given in the following tests and examples are weight percentages, parts are weight proportions, solvent ratios, dilution ratios and concentrations of liquid solutions relate, in each case, to the volume.

Abbreviations

API active pharmaceutical ingredient
h hour(s)
HCl hydrochloric acid
HEPES (4-(2-hydroxyethyl)-1-piperazineethanesulfonic acid)
HPBCD hydroxypropyl-beta-cyclodextrin
HPLC high pressure liquid chromatography
conc. concentrated
min. minutes
LO light obscuration
LAF laminar air flow
NMR nuclear magnetic resonance spectroscopy
NTU Nephelometric Turbidity Unit
PEG polyethylene glycol
PDE permissible daily exposures
$R_T$ retention time (in HPLC)
RP-HPLC reversed phase high pressure liquid chromatography
rpm revolutions per minute

Analytical Methods

Sample Reconstitution and Reconstitution Time

Prior to analysis by visual inspection, pH, osmolality, turbidity, Light Obscuration and RP-HPLC, the samples were reconstituted. For each formulation one sample was taken and the time until the full reconstitution of the lyophilized cake was measured. The lyophilized products were reconstituted under LAF conditions.

In order to take the different solid contents of the chosen formulations into account, a gravimetric determination of the water loss during lyophilization was performed. 6 vials of each formulation were weighed before and after lyophilization, and the water loss was calculated. The samples were reconstituted with the calculated volume of water. After reconstitution, samples were stored at 2-8° C.

The determined volume of water was added to the lyophilized product (into the center of the vial) by using an appropriate pipette. The vial was carefully slewed. The reconstitution time was measured as the time to achieve a full reconstitution of the lyophilized product after the liquid has been added.

Visual Inspection

The samples were inspected for the presence or absence of visible particles under gentle, manual, radial agitation for 5 seconds in front of a white background and for 5 seconds in front of a black background according to the European Pharmacopoeia ($9^{th}$ edition; monograph 2.9.20). The inspection was performed independently by two trained examiners. If visible particles were observed, they were further classified into few, medium number or many particles.

The system performance was checked by measuring the intensity of illumination with a lux meter before sample inspection.

pH

The pH value of the samples was measured with a calibrated pH meter (SevenEasy®, Mettler Toledo AG, Schwerzenbach, Switzerland) equipped with a normal ionic strength electrode (InLab Micro Pro-ISM) with temperature sensor. After every measurement, the measurement probe was thoroughly rinsed with water. The pH measurements were performed with an analysis volume of ~150 μl at n=1 and a defined temperature of 22° C.±3° C.

A 3-point calibration of the pH meter was performed on a daily basis, by using buffers with pH 7.00, pH 4.01 and pH 9.21 (InLab Solutions, Mettler Toledo AG). Additionally, the reference buffer of pH 7.00 was checked before starting the sample measurements.

Turbidity

A Hach 2100AN turbidimeter (Hach Lange, Duesseldorf, Germany) operating at 400-600 nm (using an USEPA filter) and detecting at 90° angle, was used for turbidity measurements of samples. The system is regularly calibrated by using Stablcal® turbidity standards (Hach Lange, Duesseldorf, Germany). For the measurements, 2.0 ml of samples were analyzed. The results were given in nephelometric turbidity units (NTU).

Light Obscuration (LO)

The PAMAS SVSS-C Sensor HCB-LD-25/25 (Partikelmess- und Analysensysteme GmbH, Rutesheim, Germany) was used for light obscuration measurements.

For light obscuration measurements the samples were analyzed preferably undiluted or after dilution with filtered formulation buffer to the working range of the instrument.

All measurements were performed in accordance to USP <787> low volume method. The average results for the particle concentrations were calculated based on the last three sub-runs for particles sizes ≥1, 2, 5, 10, 15, 25, 50, and 100 μm, respectively.

Prior to Each Sample Measurement, a Washing Step was Performed by Using Highly Purified Water and Verified by a Cleanliness Check. Reversed-Phase High Performance Liquid Chromatography (RP-HPLC)

RP-HPLC was used to determine the concentration of letermovir free base and potential degradation products. Table 1 gives an overview of the eluents that were used for RP-HPLC analysis.

TABLE 1

| Eluents | Preparation |
|---|---|
| Eluent A: (0.1% formic acid in water) | Add 500 μl formic acid to a volumetric flask and fill up to 500 ml with highly purified water |
| Eluent B: (0.1% formic acid in methanol) | Add 500 μl formic acid to a volumetric flask and fill up to 500 ml with methanol |

The following parameters were used for the RP-HPLC method:

Instrument: Thermo Scientific Ultimate 3000 UHPLC

Column: Agilent Zorbax Eclipse XDB C-18, 150×4.6 mm, 5 μm

Flow rate: 1.0 ml/min

Solvent A: 0.1% formic acid in water

Solvent B: 0.1% formic acid in 100% methanol

Stop time: 27 minutes

Injection volume: 5 μl

Column temperature: 35° C.

Wavelength: 260 nm

Autosampler temperature: 10° C.

Table 2 shows the gradient that was used for the RP-HPLC method.

TABLE 2

Gradient applied during RP-HPLC analysis.

| Time [min] | Eluent B [%] |
|---|---|
| 0.00 | 5.0 |
| 1.00 | 5.0 |
| 20.00 | 95.0 |
| 23.00 | 95.0 |
| 23.10 | 5.0 |
| 26.00 | 5.0 |

A reference solution of letermovir crystalline sodium trihydrate salt was freshly prepared at a target concentration of 1.5 mg/ml (corrected for letermovir free base in solution) in water. This reference solution was injected in the beginning and at the end of every sequence. A calibration curve of the reference standard was used for the quantification of Letermovir free base in solution, as long as the injection of the 1.5 ml/ml reference solution shows a complete recovery.

The samples were diluted to 1 mg/ml in water (corrected for letermovir free base in solution) and analyzed with an injection volume of 5 μl. Prior to injection, the diluted samples were centrifuged at 10,000 rpm for 3 min After each sample or reference injection, two blank injections (water) were performed to minimize sample carry-over.

Peak integration was performed manually for all API-related peaks. Peaks that were also present in blank or formulation buffer injections were neglected. Not-baseline separated peaks were split by perpendicular drop performed in the valley/at the shoulder of two peaks.

Cake Appearance

The freeze dried cakes were evaluated by visual inspection after drying. Parameters taken into consideration are compactness of the cake, shape of the cake, color and overall appearance.

Freeze-Drying Microscopy (FDM)

The behavior of the frozen formulations under vacuum was analyzed by freeze-drying microscopy (FDSC 196, Resultec).

For each formulation 2 μl of the sample was pipetted on a quartz crucible. The sample was frozen to −50° C., then vacuum was applied and the sample was heated including isothermal steps e.g. at −40° C. until collapse and melting was observed.

During the progress of collapse, images were taken in regular intervals. Collapse onset temperature ($T_{c,on}$) of the frozen solution was determined from the appearance of translucent dots or fissures behind the ice sublimation interface, based on the images.

Differential Scanning Calorimetry (DSC)

Differential scanning calorimetry (DSC) in a Mettler Toledo DSC1_943 (Mettler Toledo, Giessen, Germany) was used to determine thermal events of the frozen formulation (glass transition temperature of the maximally freeze-concentrated solution ($T_{g'}$)) and of the freeze-dried products (glass transition temperature ($T_g$)).

Karl-Fischer Titration (KF)

The water content of the lyophilized cakes was determined by using a coulometric Karl-Fischer titrator Aqua 40.00 (Analytik Jena GmbH, Jena, Germany), which was equipped with a headspace module. Freeze dried product was weighed into glass vials and heated to 120° C. in the oven connected to the reaction vessel via a tubing system. The evaporated water was transferred into the titration solution and the amount of water was determined.

X-Ray Powder Diffraction (XRD)

Wide angle X-ray powder diffraction (XRD) was used to study the morphology of lyophilized products. The X-ray diffractometer Empyrean (Panalytical, Almelo, Netherlands) equipped with a copper anode (45 kV, 40 mA, $K_{\alpha 1}$ emission at a wavelength of 0.154 nm) and a PIXcel3D detector was used. Freeze dried product was analyzed in reflection mode in the angular range from 5-45° 2θ, in order to detect the presence of crystalline and/or amorphous structures.

EXAMPLES

Example 1. Pre-Lyophilization Formulation Screening

General Procedure:

50 ml of each formulation F1-F16 were prepared by weighing the respective excipients into a washed beaker and subsequent dissolution in water by using about 80% of target volume. Following, letermovir sodium salt trihydrate was dissolved in the respective formulation buffer to a final API concentration of 20 mg/ml (corrected with a correction factor of 1.13 for Letermovir free base in solution). The pH was adjusted to the target, according to Table 3. For formulation F16, polysorbate 20 (PS20) was spiked into the pH-adjusted material to achieve a final PS20 concentration of 0.02% (w/v). The formulations were finally filled up to the target volume by using water (q.s.).

The formulations were filtered through 0.2-µm nylon-membrane syringe filters under LAF conditions.

Volumes of 14 ml were transferred into washed, sterilized and dried 20R glass vials under LAF conditions. The vials were closed with sterilized and dried rubber stoppers and crimp capped. Subsequently, the vials were used (i) to perform the time-zero analysis and (ii) for the storage stability study at room temperature.

The following pre-lyophilization formulations were studied according to the general procedure, as shown in Table 3:

TABLE 3

Studied pre-lyophilization formulations

| Sample ID | pH | Buffer system | Excipient 1 | Excipient 2 | pH adjustment |
|---|---|---|---|---|---|
| F1 | 7.5 | — | 53 mM NaCl | 150 mg/ml HP-β-CD | HCl/NaOH |
| F2 | 8.0 | 20 mM Tris | — | — | q.s. HCl |
| F3 | 8.0 | 20 mM sodium phosphate | — | — | q.s. HCl |
| F4 | 7.6 | 20 mM Tris | — | — | q.s. HCl |
| F5 | 7.6 | 20 mM sodium phosphate | — | — | q.s. HCl |
| F6 | 7.6 | 20 mM histidine | — | — | q.s. HCl |
| F7 | 7.6 | 20 mM HEPES | | | q.s. HCl |
| F8 | 8.0 | — | — | — | q.s. HCl |
| F9 | 7.6 | — | — | — | q.s. HCl |
| F10 | 7.6 | — | — | — | q.s. citric acid |
| F11 | 7.6 | — | — | — | q.s phosphoric acid |
| F12 | 7.6 | — | 50 mg/ml sucrose | 10 mg/ml L-phenylalanine | q.s. HCl |
| F13 | 7.6 | — | 60 mg/ml mannitol | — | q.s. HCl |
| F14 | 7.6 | — | 60 mg/ml sucrose | — | q.s. HCl |
| F15 | 7.6 | — | 40 mg/ml sucrose | 30 mg/ml PVP K12 | q.s. HCl |
| F16 | 7.6 | — | — | 0.02% Tween 20 | q.s. HCl |

Results

Three formulations (F3, F5 and F7) did not dissolve in the initial buffer formulation before pH adjustment. 20 mM sodium phosphate and 20 mM HEPES were not suitable buffer systems to dissolve the Letermovir sodium salt trihydrate form.

During the pH adjustment the drug substance surprisingly precipitated when citric acid and phosphoric acid (F10, F11) were used instead of HCl. After a prolonged stirring for approximately 24 hours at room temperature the precipitates were still observed.

Tween 20 as a surfactant (F16) also resulted in precipitation. After a prolonged stirring for approximately 24 hours at room temperature the precipitates were still observed.

Consequently, formulations F3, F5, F7, F10, F11 and F16 were excluded from the further investigation. The further study was performed with only 10 out of 16 planned formulations.

No changes in pH, osmolality, purity and API content (determined by RP-HPLC)) were observed in all formulations over 72 hours. The formulation used histidine buffer (F6) and buffer-free at pH 7.6 (F9) showed increasing levels of turbidity over time. Formulations of higher pH (F2 and F8) showed no visible particles after 72 h.

10 out of 16 formulations showed a clear solution after preparation and pH adjustment. HCl was the preferred acid for pH adjustment. TRIS buffer was the most suitable buffer system.

Example 2. Development of Lyophilization Formulation

The following further formulation candidates were selected based on the results of the screening according to Example 1, as shown in Table 4:

TABLE 4

Studied lyophilization formulations

| No. | API conc. (free base) | pH | Buffer system | Excipient 1 | Excipient 2 | Excipient 3 | pH adjustment | Expected pH* |
|---|---|---|---|---|---|---|---|---|
| F17 | 20 mg/ml | 9.0 | — | 70 mg/ml sucrose | — | — | — | ca. 7.8-8.0 |
| F18 | 20 mg/ml | 8.0 | — | 70 mg/ml sucrose | — | — | 0.4M HCl | ca. 7.8 |
| F19 | 20 mg/ml | 7.6 | — | 70 mg/ml PVP K12 | — | — | 0.4M HCl | ca. 7.6 |
| F20 | 20 mg/ml | 7.6 | — | 50 mg/ml PVP PF12 | 20 mg/ml Tris base | — | 0.4M HCl | ca. 7.6 |
| F21 | 20 mg/ml | 7.6 | — | 50 mg/ml PVP PF12 | 20 mg/ml L-Arginine base | — | 0.4M HCl | ca. 7.6 |
| F22 | 20 mg/ml | 8.0 | — | 40 mg/ml sucrose | 30 mg/ml PVP PF12 | — | 0.4M HCl | ca. 7.8 |
| F23 | 20 mg/ml | 7.6 | — | — | 100 mg/ml PVP PF12 | — | 0.4M HCl | ca. 7.6 |
| F24 | 20 mg/ml | 7.6 | 35 mM Tris base | 30 mg/ml sucrose | 40 mg/ml PVP PF12 | 20 mg/ml L-Arginine base | 0.4M HCl | ca. 7.6 |
| F25 | 20 mg/ml | 7.4 | 35 mM Tris base | 30 mg/ml sucrose | 40 mg/ml PVP PF12 | 20 mg/ml L-Arginine base | 0.4M HCl | ca. 7.4 |
| F26 | 20 mg/ml | 8.0 | — | 50 mg/ml sucrose | 10 mg/ml L-phenylaline | — | 0.4M HCl | ca. 7.8 |
| F27 | 20 mg/ml | 8.0 | — | 60 mg/ml mannitol | — | — | 0.4M HCl | ca. 7.8 |
| F28 | 20 mg/ml | 7.6 | — | 40 mg/ml mannitol | 20 mg/ml L-Arginine base | — | 0.4M HCl | ca. 7.6 |
| F29 | 20 mg/ml | 7.6 | — | 20 mg/ml sucrose | 50 mg/ml PVP PF12 | 0.8% poloxamer 188 | 0.4M HCl | ca. 7.6 |
| F30 | 80 mg/ml | 7.6 | — | 40 mg/ml sucrose | — | — | 0.4M HCl | ca. 7.6 |
| F31 | 20 mg/ml | 7.6 | — | 30 mg/ml PVP PF12 | 50 mg/ml L-Arginine base | — | 0.4M HCl | ca. 7.6 |

*After dilution in commercial diluents

The formulation candidates were studied according to the following general procedure:

Two hundred fifty (250) ml of each formulation were prepared by weighing the respective excipients into a washed beaker and subsequent dissolution in water by using about 80% of the target volume. Letermovir sodium trihydrate salt was then dissolved in the respective formulation buffer to a final API concentration of 20 mg/ml (corrected with a correction factor of 1.13 for Letermovir free base in solution). The pH was adjusted to the target value by the addition of 0.4 M HCl. The formulations were filled with water (q.s.) to the target volume.

The formulations were filtered by using vacuum filter systems equipped with a 0.2-μm nylon-membrane.

Volumes of 13 ml were transferred into washed, sterilized and dried 20R glass vials under LAF conditions. The vials were partly closed with sterilized and dried rubber stoppers and lyophilized by using a standard lyophilization cycle, as described in Table 5:

TABLE 5

Lyophilization cycle

| # No | Step | Time [hh:mm:ss] | Shelf temperature [° C.] | Pressure [mbar] | Total time [h] | Ramp (° C./min) |
|---|---|---|---|---|---|---|
| 1 | loading and equilibration at 5° C. | 0:00:00 | 5 | 1,000 | 0.0 | |
| 2 | Freezing | 1:40:00 | −45 | 1,000 | 1.7 | 0.50 |
| 3 | Freezing | 11:20:00 | −45 | 1,000 | 13.0 | |
| 4 | primary drying | 0:30:00 | −45 | 0.1 | 13.5 | |
| 5 | primary drying | 0:40:00 | −25 | 0.1 | 14.2 | 0.50 |

TABLE 5-continued

Lyophilization cycle

| # No | Step | Time [hh:mm:ss] | Shelf temperature [° C.] | Pressure [mbar] | Total time [h] | Ramp (° C./min) |
|---|---|---|---|---|---|---|
| 6 | primary drying | 176:15:00 | −25 | 0.1 | 74.2 | |
| 7 | secondary drying | 9:00:00 | 30 | 0.1 | 83.2 | 0.10 |
| 8 | secondary drying | 10:00:00 | 30 | 0.1 | 93.2 | |
| 9 | Aeration | 0:30:00 | 30 | 800 | 93.7 | |
| 10 | Stoppering | 0:01:00 | 30 | 800 | 93.7 | |
| 11 | Storage | 0:30:00 | 5 | 1,000 | 94.2 | |

After lyophilization, all vials were crimp-capped, labeled, analyzed and placed on stability over 1 month under 25° C./60% relative humidity and 40° C./75% relative humidity.

Results

Two out of five formulations containing arginine (F28 and F31) precipitated during the pH adjustment. After a prolonged stirring for approximately 24 hours at room temperature the precipitates were still observed.

The formulation containing phenylalanine did not require any pH adjustment.

Consequently, F28 and F31 were excluded from the further investigations. The study was continued with 13 out of 15 planned formulations.

Arginine-containing formulations (F21, F24 and F25) showed increased turbidity levels. Arginine did not enhance API solubility.

The formulation with Poloxamer (F29) showed least precipitation during pH adjustment process which may result in improved manufacturability of such formulations.

Except for F27, all formulations showed an amorphous cake matrix

No changes in DSC, pH, cake appearance, water content (determined by Karl Fischer titration), osmolality, purity, and API content (determined by RP-HPLC), XRD were observed in any of the exemplary formulations over 1 month.

Example 3. Reconstitution of Lyophilization Formulations

The lyophilisation formulations of Example 2 were further reconstituted according to the following general procedure:

Water for injection was added to the lyophilizates. The addition was done after removal of the flip-off cap by using a 20-ml syringe and a 20G needle (40 mm in length). The content of the vial was carefully homogenized by gentle manual rotation. In parallel, one empty infusion bag was filled with 288 ml of the two parenteral admixture diluents (5% glucose and Ringer's lactated solution), respectively, by using a 50-ml syringe and a Mini-Spike.

A volume of 12 ml of the reconstituted lyophilizate with the concentration of 20 mg/ml was removed per vial, by using a 20-ml syringe and a 20G needle (40 mm in length). The volume was then directly injected into the diluent-containing infusion bag resulting in a final concentration of 0.8 mg/ml.

Results

All formulations reconstituted in Ringer's lactated solution were in the physiological pH range (7.4-7.8).

The formulation with a higher API concentration 80 mg/mL (F30) showed substantially prolonged reconstitution time of ca. 33 minutes. All other formulations reconstituted in between 1 to 5 minutes.

The samples of lyophilizates stored on stability were reconstituted according to the general procedure.

No changes in reconstitution time, turbidity, pH, osmolality and purity (determined by RP-HPLC) were observed in any of the exemplary formulations over 1 month.

Example 4. Further Formulations Optimization

The following further formulation candidates were selected based on the results of the previous examples, as shown in Table 6:

TABLE 6

Final formulation candidates

| No. | API conc. (free base eq.) | pH | Buffer system | Excipient 1 | Excipient 2 | Excipient 3 | pH adjustment |
|---|---|---|---|---|---|---|---|
| F32 | 20 mg/ml | 7.8 | — | 60 mg/ml mannitol | — | — | 0.4M HCl |
| F33 | 20 mg/ml | 7.8 | — | 60 mg/ml sucrose | — | — | 0.4M HCl |
| F34 | 20 mg/ml | 7.8 | — | 30 mg/ml sucrose | 30 mg/ml PVP PF12 | 0.8% poloxamer 188 | 0.4M HCl |
| F35 | 20 mg/ml | 7.8 | 35 mM Tris-HCl | 30 mg/ml sucrose | 30 mg/ml PVP PF12 | — | 0.4M HCl |
| F36 | 20 mg/ml | 7.8 | — | 50 mg/ml sucrose | 20 mg/ml phenylalanine | — | 0.4M HCl |

The lyophilizates were prepared according to the general procedure of Example 2. After lyophilization, all vials were crimp-capped, labeled, analyzed and placed on stability over 3 months under 25° C./60% relative humidity and 40° C./75% relative humidity.

No changes in DSC, pH, cake appearance, water content (determined by Karl Fischer tirration), osmolality, purity, and API content (determined by RP-HPLC), XRD were observed in any of the exemplary formulations over 3 months.

The lyophilizates were reconstituted according to the general procedure of Example 3.

The formulation containing phenylalanine (F36) showed the reconstitution time of more than 10 minutes. All other formulations were reconstituted in less than 2 minutes.

No changes in reconstitution time, turbidity, pH, osmolality and purity (determined by RP-HPLC) were observed in any of the exemplary formulations over 3 months.

Exemplary Formulation Candidates for Intravenous Application

Based on the results of the examples 1-4, formulations F32, F33, F34 and F35 were identified as suitable for intravenous application. Amongst these candidates, F32 and F33 were identified to be suitable for intravenous application to neonates due to permissible daily exposures acceptable for intravenous formulation in neonates for the different excipients as outlined in Table 7:

TABLE 7

Permissible daily exposures for certain excipients

| Excipient | PDE |
|---|---|
| Sucrose | 11.3 mg/day |
| Lactose | 5.7 mg/day |
| Trehalose | 25.8 mg/day |
| Mannitol | 75 mg/day |
| Polyvinylpyrrolidone PF12 | Not allowed to be used in neonatal population due to potential risk |
| Poloxamer | 11.3 mg/day |

Example 5. Development of Excipient-Free Formulation 0.3164 g of letermovir sodium trihydrate salt was directly weighed into a washed, sterilized and dried 20R glass vial. Taking a correction factor of 1.13 for the crystalline trihydrate salt into account, this was equivalent to 280 mg of letermovir free base per vial. Six vials were prepared accordingly. The vials were stoppered and crimp capped.

14 ml of water for injection were added to each 20R vial containing 280 mg of Letermovir free base resulting in concentration of 20 mg/ml. Water for injection was added after removal of the flip-off disk from the vial by using a 20-ml disposable syringe plus a 20G needle of 40 mm length.

The content of the vial was carefully homogenized by gentle manual rotation. In parallel, 2 empty infusion bags were filled with 288 ml of each parenteral admixture diluents (Ringer's lactate, 0.9% saline solution and 5% dextrose solution, respectively) by using a 50-ml syringe and a Mini-Spike. 12 ml of the content of the vial was withdrawn by using a 20-ml disposable syringe plus a 20G needle of 40 mm length. The total volume of 12 ml was directly injected into the diluent containing infusion bag. After the injection, the content of the bag was carefully homogenized by gentle manual rotation. Two independent preparations of each diluent were used, i.e., in total 6 infusion bags were prepared. Following, the prepared infusion bags were put on storage at room temperature (protected from light) and another sample was analyzed after 24 hours (T24 h).

None of the reconstituted formulations precipitated over 24 hours based on a visual inspection.

For the solution reconstituted with Ringer's lactate a pH of 7.8 was observed. Surprisingly no pH adjustment was necessary.

The pH value for the other two diluents was slightly higher (pH 8.0).

The invention claimed is:

1. A method for producing a liquid pharmaceutical composition comprising a sodium salt of letermovir of formula (I)

(I)

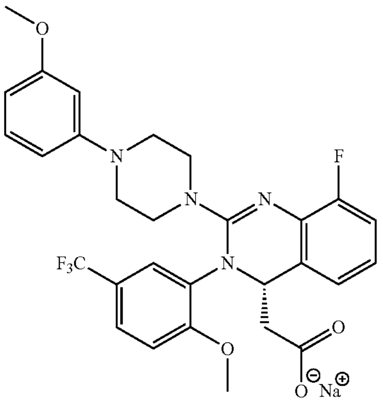

or a solvate thereof comprising the following steps:

i) providing a solution of a sodium salt of letermovir or a solvate thereof at a concentration in the range of from 20 to 100 mg/mL with respect to letermovir free base and at least one excipient selected from the group consisting of carbohydrates, amino acids, polyalkoxy compounds, and polyvinylpyrrolidone (PVP), in a physiologically acceptable diluent, wherein said solution is essentially free from any additional buffer and any complexing solubilizing agents selected from the group consisting of polyethylene glycol (PEG), lysine, arginine, and hydroxypropyl-beta-cyclodextrin (HPBCD);

optionally adjusting the pH of the solution obtained in step i to a range of from 7 to 8; and optionally filtering the obtained solution.

2. The method according to claim 1, wherein the sodium salt of letermovir is in the amorphous form, the solvate of the sodium salt of letermovir, a crystalline monohydrate of the sodium salt of letermovir, or a crystalline trihydrate of the sodium salt of letermovir.

3. A method comprising: freeze-drying the obtained solution according to claim 1 to provide a lyophilizate.

4. The method according to claim 3, further comprising reconstituting said lyophilizate in a parenterally acceptable diluent which is essentially free from complexing solubilizing agents selected from the group consisting of PEG, lysine, arginine, and hydroxypropyl-beta-cyclodextrin (HPBCD).

5. A liquid pharmaceutical composition comprising a sodium salt of letermovir of formula (I)

(I)

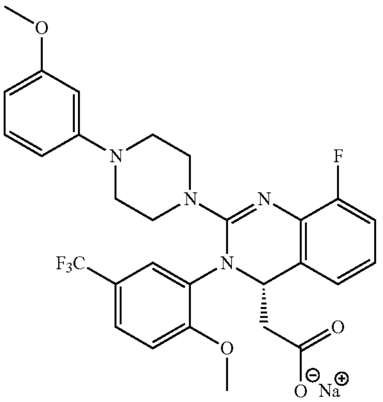

or a solvate thereof and at least one excipient selected from the group consisting of carbohydrates, amino acids, polyalkoxy compounds, and polyvinylpyrrolidone, dissolved in a physiologically acceptable diluent at a concentration in the range of from 20 to 100 mg/mL with respect to letermovir free base wherein the liquid pharmaceutical composition is essentially free from complexing solubilizing agents selected from the group consisting of PEG, lysine, arginine, and hydroxypropyl-beta-cyclodextrin (HPBCD).

6. The liquid pharmaceutical composition according to claim 5, wherein the excipient is a polyalkoxy compound, and the composition is essentially free from other complexing solubilizing agents.

7. The liquid pharmaceutical composition according to claim 5, wherein the excipient is mannitol or sucrose or a combination thereof.

8. The liquid pharmaceutical composition according to claim 5, further comprising a buffer.

9. The liquid pharmaceutical composition according to claim 5, further comprising HCl.

10. The liquid pharmaceutical composition according to claim 5 having a pH in the range of from 7 to 8.

11. A liquid pharmaceutical composition obtainable by the method as defined in claim 1.

12. The liquid pharmaceutical composition according to claim 5 which is suitable for oral application.

13. A solid pharmaceutical composition comprising a sodium salt of letermovir of formula (I)

(I)

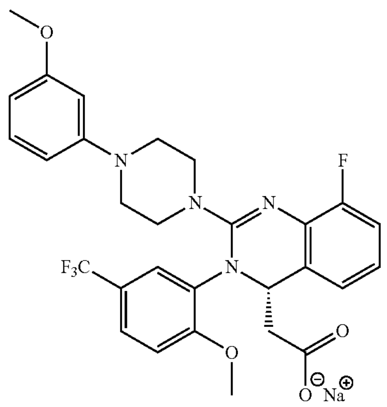

or a solvate thereof, and at least one excipient selected from the group consisting of carbohydrates, amino acids, polyalkoxy compounds, and polyvinylpyrrolidone, wherein said solid pharmaceutical composition is essentially free from complexing solubilizing agents selected from the group consisting of PEG, lysine, arginine, and hydroxypropyl-beta-cyclodextrin (HPBCD), and is capable of providing a solution when being dissolved in water without any additional buffer and without any additional complexing solubilizing agents selected from the group consisting of PEG, lysine, arginine, and hydroxypropyl-beta-cyclodextrin (HPBCD), wherein said solution comprises the sodium salt of letermovir or the solvate thereof at a concentration in the range of from 20 to 100 mg/mL with respect to letermovir free base and exhibits a pH in the range of from 7 to 8.

14. The solid pharmaceutical composition according to claim 13 which is a lyophilizate.

15. A solid pharmaceutical composition obtainable by the method as defined in claim 3.

16. A liquid pharmaceutical composition comprising the solid pharmaceutical composition as defined in claim 13, dissolved in a first parenterally acceptable diluent which is essentially free from complexing solubilizing agents selected from the group consisting of PEG, lysine, arginine, and hydroxypropyl-beta-cyclodextrin (HPBCD), at a concentration in the range of from 20 to 100 mg/mL with respect to letermovir free base.

17. The liquid pharmaceutical composition according to claim 16, wherein the liquid pharmaceutical composition is diluted in a second parenterally acceptable diluent which is essentially free from complexing solubilizing agents selected from the group consisting of PEG, lysine, arginine, and hydroxypropyl-beta-cyclodextrin (HPBCD), to a concentration which is acceptable for intravenous (IV) injection or infusion, wherein said first and said second parenterally acceptable diluents can be identical or different from each other.

18. The liquid pharmaceutical composition according to claim 16 having a pH in the range of from 7 to 8.

19. A liquid pharmaceutical composition obtainable by the method as defined in claim 4.

20. The liquid pharmaceutical composition according to claim 5, having a stability in accordance with ICH Q1A (R2) covering climate zones I to IV.

21. A method for treatment of a virus infection by a member of the herpes viridae group, comprising administering to an infected subject the liquid pharmaceutical composition according to claim 5.

22. A method for treatment of a virus infection by a member of the herpes viridae group, comprising administering to an infected subject the solid pharmaceutical composition according to claim 13.

23. A method for treatment of a virus infection by a member of the herpes viridae group, comprising administering to an infected subject the liquid pharmaceutical composition according to claim 16.

24. The liquid pharmaceutical composition obtainable by the method as defined in claim 2.

25. The method according to claim 1, wherein the at least one excipient is selected from sucrose, mannitol, phenylalanine, poloxamer 188, and polyvinylpyrrolidone (PVP), the physiologically acceptable diluent is a parenterally acceptable diluent, the solution is essentially free from any additional buffer and any complexing solubilizing agents selected from the group consisting of PEG, lysine, arginine, and cyclodextrins, and HCl is used for adjusting the pH of the solution to a range of from 7 to 8.

26. The method according to claim 25, wherein polyvinylpyrrolidone is PVP PF12.

27. The method according to claim 3, further comprising reconstituting said lyophilizate in a parenterally acceptable diluent which is essentially free from complexing solubilizing agents selected from the group consisting of PEG, lysine, arginine, and cyclodextrins.

28. The liquid pharmaceutical composition according to claim 5, wherein the physiologically acceptable diluent is a parenterally acceptable diluent, and the liquid pharmaceutical composition is essentially free from complexing solubilizing agents selected from the group consisting of PEG, lysine, arginine, and cyclodextrins, physiologically acceptable diluent at a concentration in the range of from 20 to 100 mg/mL with respect to letermovir free base.

29. The liquid pharmaceutical composition according to claim 5, wherein the at least one excipient is selected from sucrose, mannitol, phenylalanine, poloxamer 188, and polyvinylpyrrolidone (PVP).

30. The method according to claim 29, wherein polyvinylpyrrolidone is PVP PF12.

31. The liquid pharmaceutical composition according to claim 6, wherein the polyalkoxy compound is a poloxamer.

32. The liquid pharmaceutical composition according to claim 6, wherein the polyalkoxy compound is poloxamer 188.

33. The liquid pharmaceutical composition according to claim 5, wherein the buffer is tris hydroxy aminomethane (Tris).

34. The solid pharmaceutical composition according to claim 13, wherein said solid pharmaceutical composition is essentially free from complexing solubilizing agents selected from the group consisting of PEG, lysine, arginine, and cyclodextrins, said solid pharmaceutical composition is capable of providing a solution when being dissolved in water without any additional buffer and without any additional complexing solubilizing agents selected from the group consisting of PEG, lysine, arginine, and cyclodextrins, and the solution exhibits a pH in the range of 7.4 to 7.8.

35. A liquid pharmaceutical composition comprising the solid pharmaceutical composition as defined in claim 13, dissolved in a first parenterally acceptable diluent which is essentially free from complexing solubilizing agents selected from the group consisting of PEG, lysine, arginine, and cylcodextrins, at a concentration in the range of from 20 to 100 mg/mL with respect to letermovir free base.

36. The liquid pharmaceutical composition according to claim 34, wherein the liquid pharmaceutical composition is diluted in a second parenterally acceptable diluent which is essentially free from complexing solubilizing agents selected from the group consisting of PEG, lysine, arginine, and clycodextrins, to a concentration which is acceptable for intravenous (IV) injection or infusion, wherein said first and said second parenterally acceptable diluents can be identical or different from each other.

37. A method for treatment of a human cytomegalovirus (HCMV) infection comprising administering to an infected subject the liquid pharmaceutical composition according to claim 5.

38. A method for the treatment of a human cytomegalovirus (HCMV) infection comprising administering to an infected subject the solid pharmaceutical composition according to claim 13.

39. A method for the treatment of a human cytomegalovirus (HCMV) infection comprising administering to an infected subject the liquid pharmaceutical composition according to claim 16.

40. A method for prevention of a virus infection by a member of the herpes viridae group comprising administering to a subject the liquid pharmaceutical composition according to claim 5.

41. A method for prevention of a virus infection by a member of the herpes viridae group comprising administering to a subject the solid pharmaceutical composition according to claim 13.

42. A method for prevention of a virus infection by a member of the herpes viridae group comprising administering to a subject the liquid pharmaceutical composition according to claim 16.

43. A method for prevention of a human cytomegalovirus (HCMV) infection comprising administering to a subject the liquid pharmaceutical composition according to claim 5.

44. A method for prevention of a human cytomegalovirus (HCMV) infection comprising administering to a subject the solid pharmaceutical composition according to claim 13.

45. A method for prevention of a human cytomegalovirus (HCMV) infection comprising administering to a subject the liquid pharmaceutical composition according to claim 16.

46. The solid pharmaceutical composition according to claim 13, wherein the at least one excipient is selected from carbohydrates, amino acids and polyalkoxy compounds.

47. The solid pharmaceutical composition according to claim 13, wherein the at least one excipient is selected from sucrose, mannitol, phenylalanine, poloxamer 188, and polyvinylpyrrolidone.

48. The solid pharmaceutical composition according to claim 13, wherein the at least one excipient is selected from sucrose, mannitol, phenylalanine and poloxamer 188.

* * * * *